US008070831B2

(12) United States Patent
Simonet et al.

(10) Patent No.: US 8,070,831 B2
(45) Date of Patent: Dec. 6, 2011

(54) COMPOSITION COMPRISING AT LEAST ONE SOLID FATTY ALCOHOL, DYEING OR LIGHTENING PROCESS USING SAME AND DEVICES

(75) Inventors: Frédéric Simonet, Clichy (FR); Franck Clement, Sainte Genevieve des Bois (FR); Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,593

(22) Filed: Dec. 18, 2009

(65) Prior Publication Data
US 2010/0247465 A1 Sep. 30, 2010

Related U.S. Application Data

(60) Provisional application No. 61/151,966, filed on Feb. 12, 2009.

(30) Foreign Application Priority Data

Dec. 19, 2008 (FR) ...................................... 08 07313

(51) Int. Cl.
*A61Q 5/10* (2006.01)
(52) U.S. Cl. .......................... 8/405; 8/406; 8/435; 8/611
(58) Field of Classification Search .............. 8/405, 406, 8/435, 611
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,826,681 A | 5/1989 | Jacquet et al. | |
| 4,845,293 A | 7/1989 | Junino et al. | |
| 5,021,066 A | 6/1991 | Aeby et al. | |
| 5,259,849 A | 11/1993 | Grollier et al. | |
| 5,364,414 A | 11/1994 | Lang et al. | |
| 5,817,155 A | 10/1998 | Yasuda et al. | |
| 6,010,541 A | 1/2000 | De La Mettrie | |
| 6,074,439 A | 6/2000 | De La Mettrie et al. | |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,251,378 B1 | 6/2001 | Laurent et al. | |
| 6,260,556 B1 | 7/2001 | Legrand et al. | |
| 6,277,154 B1 * | 8/2001 | Lorenz | 8/405 |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,645,258 B2 | 11/2003 | Vidal et al. | |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |
| 7,135,046 B2 | 11/2006 | Audousset | |
| 7,153,331 B2 | 12/2006 | Desenne et al. | |
| 7,217,298 B2 | 5/2007 | Legrand et al. | |
| 7,285,137 B2 | 10/2007 | Vidal et al. | |
| 7,442,215 B2 | 10/2008 | Audousset et al. | |
| 7,458,993 B2 | 12/2008 | Cottard et al. | |
| 7,494,513 B2 | 2/2009 | Kravtchenko et al. | |
| 7,575,605 B2 | 8/2009 | Legrand | |
| 7,651,533 B2 | 1/2010 | Legrand | |
| 7,651,536 B2 | 1/2010 | Cottard et al. | |
| 7,740,663 B2 | 6/2010 | De La Mettrie et al. | |
| 7,766,977 B2 | 8/2010 | Cottard | |
| 7,799,095 B2 | 9/2010 | Mario et al. | |
| 2002/0189034 A1 | 12/2002 | Kitabata et al. | |
| 2003/0064494 A1 | 4/2003 | Kumar et al. | |
| 2003/0190297 A1 | 10/2003 | Narasimhan et al. | |
| 2003/0226217 A1 | 12/2003 | Bowes et al. | |
| 2004/0103488 A1 | 6/2004 | Yamashita et al. | |
| 2004/0105830 A1 | 6/2004 | Boswell et al. | |
| 2004/0181883 A1 | 9/2004 | Legrand et al. | |

(Continued)

FOREIGN PATENT DOCUMENTS

CA      1 268 421      5/1990

(Continued)

OTHER PUBLICATIONS

Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.

(Continued)

*Primary Examiner* — Eisa Elhilo
(74) *Attorney, Agent, or Firm* — Finnegan, Henderson, Farabow, Garrett & Dunner, LLP

(57) ABSTRACT

The present disclosure relates to compositions for dyeing or lightening human keratin fibers, dyeing or lightening processes using the compositions, and two-compartment or three-compartment devices comprising the compositions, wherein the compositions comprise, in a cosmetically acceptable medium: at least 25% by weight of a mixture of fatty substances comprising at least one fatty alcohol that is solid at ambient temperature; at least one oxidizing agent; and optionally at least one basifying agent.

24 Claims, No Drawings

U.S. PATENT DOCUMENTS

| | | | |
|---|---|---|---|
| 2004/0221400 A1 | 11/2004 | Cotteret et al. | |
| 2004/0226110 A1 | 11/2004 | LeGrand | |
| 2004/0235700 A1 | 11/2004 | Legrand et al. | |
| 2005/0129652 A1 | 6/2005 | Keller et al. | |
| 2005/0165705 A1 | 7/2005 | Lauper et al. | |
| 2005/0196367 A1 | 9/2005 | Ohta et al. | |
| 2006/0042023 A1 | 3/2006 | Machida | |
| 2006/0075580 A1* | 4/2006 | Chan et al. | 8/405 |
| 2006/0137111 A1 | 6/2006 | Au et al. | |
| 2006/0242773 A1 | 11/2006 | Kravtchenko et al. | |
| 2006/0260071 A1 | 11/2006 | Legrand | |
| 2006/0265817 A1* | 11/2006 | Legrand | 8/405 |
| 2007/0006397 A1 | 1/2007 | Schmenger et al. | |
| 2007/0033743 A1 | 2/2007 | Kravtchenko | |
| 2007/0104672 A1 | 5/2007 | Decoster et al. | |
| 2007/0169285 A1 | 7/2007 | Narasimhan et al. | |
| 2007/0275927 A1 | 11/2007 | Philippe | |
| 2007/0277331 A1 | 12/2007 | Goldstein et al. | |
| 2008/0016627 A1 | 1/2008 | Cottard et al. | |
| 2008/0071092 A1 | 3/2008 | Vidal et al. | |
| 2008/0229512 A1 | 9/2008 | Syed et al. | |
| 2008/0256724 A1 | 10/2008 | Bolton et al. | |
| 2009/0007347 A1 | 1/2009 | Cottard et al. | |
| 2009/0060855 A1 | 3/2009 | Boche et al. | |
| 2009/0151086 A1 | 6/2009 | Brun | |
| 2009/0151087 A1 | 6/2009 | Mario et al. | |
| 2009/0158533 A1 | 6/2009 | Hercouet | |
| 2009/0162309 A1 | 6/2009 | Hercouet et al. | |
| 2009/0191142 A1 | 7/2009 | Hercouet et al. | |
| 2010/0162492 A1 | 7/2010 | Hercouet et al. | |
| 2010/0175705 A1 | 7/2010 | Hercouet et al. | |
| 2010/0186177 A1 | 7/2010 | Hercouet et al. | |
| 2010/0199441 A1 | 8/2010 | Hercouet et al. | |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 | 4/2009 |
| EP | 2 072 034 | 6/2009 |
| EP | 2 072 035 | 6/2009 |
| EP | 2 072 036 | 6/2009 |
| EP | 2 198 842 | 6/2010 |
| EP | 2 198 843 | 6/2010 |
| EP | 2 198 849 | 6/2010 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| FR | 2 940 054 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |

| | | |
|---|---|---|
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 20 05 076, dated Aug. 6, 1970.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2007/006418, dated Jan. 18, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.

French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
Copending U.S. Appl. No. 12/976,093, filed Dec. 22, 2010.
Copending U.S. Appl. No. 12/976,124, filed Dec. 22, 2010.
Copending U.S. Appl. No. 12/976,150, filed Dec. 22, 2010.
Copending U.S. Appl. No. 12/976,173, filed Dec. 22, 2010.
English language Abstract of WO 2007/006418, dated Jan. 18, 2007.
European Search Report for EP 10 15 5935, dated Oct. 8, 2010.
European Search Report for EP 10 19 5262, dated Apr. 1, 2011.
French Search Report for FR 09/59388, dated Aug. 3, 2010.
French Search Report for FR 09/59391, dated Sep. 16, 2010.
French Search Report for FR 09/59433, dated Sep. 24, 2010.
French Search Report for FR 09/59434, dated Sep. 24, 2010.
LookChem, poly[(dimethyliminio)-1,1,6-hexanediylchloride (1:2)], pp. 1-2, accesses Mar. 7, 2011.
Notice of Allowance mailed Apr. 1, 2011, in U.S. Appl. No. 12/642,506.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed Jan. 28, 2011, in U.S. Appl. No. 12/642,592.
Notice of Allowance mailed Mar. 9, 2011, in U.S. Appl. No. 12/642,473.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Office Action mailed Dec. 17, 2010, in co-pending U.S. Appl. No. 12/642,451.
Office Action mailed Jun. 8, 2011, in co-pending U.S. Appl. No. 12/339,781.
Office Action mailed Mar. 16, 2011, in co-pending U.S. Appl. No. 12/642,583.
Office Action mailed Mar. 29, 2011, in co-pending U.S. Appl. No. 12/642,468.
P.R. Canterbery et al., International Cosmetic Ingredient Dictionary and Handbook, vol. 1, p. 759 (2002).
Ullmann's Encyclopedia of Industrial Chemistry, "Hair Preparations," Wiley-VCH Verlag GnbH & Co., KGaA, Weinheim, p. 20 (2006).

* cited by examiner

US 8,070,831 B2

COMPOSITION COMPRISING AT LEAST ONE SOLID FATTY ALCOHOL, DYEING OR LIGHTENING PROCESS USING SAME AND DEVICES

CROSS-REFERENCE TO RELATED APPLICATIONS

This application claims benefit of priority under 35 U.S.C. §119 to French Patent Application No. 0807313, filed Dec. 19, 2008, and the benefit of U.S. Provisional Application No. 61/151,966, filed Feb. 12, 2009, the content of all of which is incorporated herein by reference.

One subject of the present invention is a composition for dyeing or lightening human keratin fibres comprising, besides the dyes, preferably oxidation dyes, when they are present, and the oxidizing agent, a high content of fatty substances comprising at least one fatty alcohol that is solid at ambient temperature.

The invention also relates to a dyeing or lightening process using it and to multi-compartment devices.

Among the methods for dyeing human keratin fibres, such as the hair, mention may be made of oxidation dyeing or permanent dyeing. More particularly, this dyeing method uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds, which, when combined with oxidizing products, can give access to coloured species.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

It is also possible to add to these compositions direct dyes, which are coloured and colouring molecules that have affinity for fibres. The direct dyes generally used are chosen from nitrobenzene, anthrax-quinone, nitropyridine, azo, methine, azomethine, xanthene, acridine, azine and triarylmethane direct dyes. The presence of such compounds enables the obtained coloration to be further enriched with tints or enables the chromaticity of the obtained coloration to be increased.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloration, via an oxidative condensation reaction between the oxidation dyes.

The oxidation dye must moreover satisfy a certain number of requirements. Thus, it must be free of toxicological drawbacks, it must enable shades to be obtained in the desired intensity and it must show the resistance to external attacking factors such as light, bad weather, washing, permanent waving, perspiration and rubbing.

The dyes must also be able to cover grey hair and, finally, they must be as unselective as possible, i.e. they must produce the smallest possible colour differences along the same keratin fibre, which generally comprises areas that are differently sensitized (i.e. damaged), from its end to its root.

The compositions obtained must also have good mixing and application properties, and especially good rheological properties so as not to run down the face, onto the scalp or beyond the areas that it is proposed to dye, when they are applied.

As regards the processes for lightening keratin fibres, aqueous compositions are used that comprise at least one oxidizing agent, under alkaline pH conditions in the vast majority of cases. The role of this oxidizing agent is to break down the melanin of hair, which depending on the nature of the oxidizing agent present, results in a more or less pronounced lightening of the fibres.

Many attempts have been made in the field of hair dyeing in order to improve the dyeing properties, for example using adjuvants. However, the choice of these adjuvants is difficult insofar as they must improve the dyeing properties of dye compositions without harming the other properties of these compositions. In particular, these adjuvants must not harm the keratin fibre-lightening properties and the dye application properties.

Similar problems are faced in the case of lightening compositions where the addition of particular adjuvants must not harm the lightening properties of the composition nor the application properties especially rheological properties, of the composition.

The objective of the present invention is to obtain novel compositions for the oxidation dyeing or the lightening of keratin fibres, which do not have the drawbacks of the prior art.

More particularly, the aim of the present invention is to obtain compositions for the oxidation dyeing of keratin fibres, with improved dyeing properties, which can achieve the desired lightening and which are easy to mix and to apply, and which especially do not run but remain localized at the point of application. The term "improved dyeing properties" in particular means an improvement in the power/intensity and/or uniformity of the dyeing result.

Another objective of the invention is also to obtain lightening compositions that make it possible to achieve the desired lightening, which are easy to mix and to apply, and which especially do not run but remain localized at the point of application.

These objectives and others are achieved by the present invention, one subject of which is thus a compositing for dyeing or lightening human keratin fibres, characterized in that it comprises, in a cosmetically acceptable medium:
 (a) at least 25% by weight of a mixture of fatty substances comprising one or more fatty alcohols that are solid at ambient temperature; the mixture of fatty substances comprising at least one additional fatty substance chosen from $C_6$-$C_{16}$ lower alkanes, non-silicone oils of animal, mineral or synthetic origin, fatty alcohols other than fatty alcohols that are solid at ambient temperature, esters of a fatty acid and/or of a fatty alcohol, non-silicone waxes, silicones, or mixtures thereof;
 (b) one or more oxidizing agents; and
 (c) optionally one or more basifying agents.

It also relates to a process for dyeing or lightening human keratin fibres that comprises using the aforementioned composition.

One subject of the invention is likewise a two-compartment device comprising, in one compartment, a first composition comprising one or more fatty substances, optionally one or more dyes, preferably oxidation dyes, and in the other compartment, a second composition comprising one or more oxidizing agents; the first composition and/or the second composition comprising at least one fatty alcohol that is solid at ambient temperature and optionally one or more basifying agents; the compositions of the two compartments being intended to be mixed in order to give the composition according to the invention, just before application to the human keratin fibres.

The invention lastly relates to a three-compartment device comprising, in one compartment, a first composition comprising one or more fatty substances, in another compartment, a second composition comprising one or more dyes, preferably oxidation dyes and/or one or more basifying agents and/or mixtures thereof, and in the last compartment, a third composition comprising one or more oxidizing agents; the first and/or second and/or third composition comprising at least one fatty alcohol that is solid at ambient temperature; the compositions of the three compartments being intended to be mixed in order to give the composition according to the invention, just before application to the human keratin fibres.

Other features and advantages of the invention will appear more clearly on reading the description and examples that follow.

In the text herein below, unless otherwise indicated, the limits of a range of values are included in that range.

The human keratin fibres treated by the process according to the invention are preferably hair.

When the composition according to the invention is used for lightening, it does not comprise a direct dye or an oxidation dye precursor (bases and couplers) that are customarily used for dyeing human keratin fibres or else, if it does comprise any, their total content does not exceed 0.005% by weight relative to the weight of the composition. Specifically, at such a content, only the composition would possibly be dyed, that is to say that no coloration effect would be observed on the keratin fibres.

Preferably, the lightening process is performed without oxidation base or coupler or direct dye.

As indicated previously, the dyeing or lightening composition according to the invention comprises at least 25% by weight of one or more fatty substances, at least one of which is a fatty alcohol that is solid at ambient temperature (25° C., 760 mmHg).

The fatty alcohols that are solid at ambient temperature and that are suitable for the implementation of the invention are more particularly chosen from saturated or unsaturated, linear or branched alcohols comprising from 8 to 30 carbon atoms. Preferably, the fatty alcohol or alcohols are chosen from saturated linear fatty alcohols comprising from 8 to 30 and preferably from 10 to 22 carbon atoms. Moreover, it is understood that the fatty alcohols do not comprise $C_2$-$C_3$ oxyalkylenated unit(s) or glycerylated unit(s). Mention may be made, for example, of cetyl alcohol, stearyl alcohol, behenyl alcohol and a mixture thereof (cetyl-stearyl alcohol).

More particularly, the content of fatty alcohols that are solid at ambient temperature, in the composition according to the invention, is between 0.2 and 50% by weight, preferably between 0.5 and 30% by weight, and more particularly still between 1 and 15% by weight relative to the weight of the composition.

The composition of the invention may comprise other fatty substances in order to reach the required amount of at least 25% by weight. The composition according to the invention has, more particularly, a total content of fatty substances ranging from 25 to 85% by weight, preferably from 25 to 65%, and more particularly still from 30 to 55% by weight relative to the total weight of the composition.

The expression "fatty substance" is understood to mean an organic compound that is insoluble in water at ordinary temperature (25° C.) and at atmospheric pressure (760 mmHg) (solubility of less than 5%, preferably 1% and even more preferably 0.1%). They have in their structure at least one hydrocarbon-based chain comprising at least 6 carbon atoms or a sequence of at least two siloxane groups. Moreover, the fatty substances are generally soluble in organic solvents under the same temperature and pressure conditions, such as for example chloroform, ethanol, benzene, liquid petroleum jelly or decamethylcyclopentasiloxane.

More particularly, the fatty substances other than fatty alcohols that are solid at ambient temperature are not fatty acids.

They are more particularly chosen from $C_6$-$C_{16}$ lower alkanes, non-silicone oils of animal, mineral or synthetic origin, fatty alcohols other than fatty alcohols that are solid at ambient temperature, esters of a fatty acid and/or of a fatty alcohol, non-silicone waxes, silicones, or mixtures thereof.

It is recalled that, for the purposes of the invention, the fatty alcohols, fatty esters and fatty acids more particularly contain at least one linear or branched, saturated or unsaturated hydrocarbon-based group containing 6 to 30 carbon atoms, which is optionally substituted, in particular with one or more hydroxyl groups (in particular 1 to 4). If they are unsaturated, these compounds may comprise one to three conjugated or non-conjugated carbon-carbon double bonds.

As regards the $C_6$-$C_{16}$ lower alkanes, they are linear or branched, or possibly cyclic. Examples that may be mentioned include hexane, undecane, dodecane, tridecane and isoparaffins such as isohexadecane and isodecane.

As non-silicone oils of animal, plant, mineral or synthetic origin that may be used in the composition of the invention, examples that may be mentioned include:

hydrocarbon-based oils of animal origin, such as perhydrosqualene;

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil;

linear or branched hydrocarbons of mineral or synthetic origin, containing more than 16 carbon atoms, such as volatile or non-volatile liquid paraffins, and derivatives thereof, petroleum jelly, liquid petroleum jelly, polydecenes, hydrogenated polyisobutenes such as Parleam®; preferably liquid paraffins, petroleum jelly, liquid petroleum jelly, polydecenes, hydrogenated polyisobutenes such as Parleam®;

fluoro oils, for instance perfluoromethylcyclo-pentane and perfluoro-1,3-dimethylcyclohexane, sold under the names Flutec® PC1 and Flutec® PC3 by the company BNFL Fluorochemicals; perfluoro-1,2-dimethyl-cyclobutane; perfluoroalkanes such as dodecafluoro-pentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols other than the aforementioned fatty alcohols that are solid at ambient temperature and that are suitable for use in the invention may more particularly be chosen from branched or unsaturated alcohols containing from 8 to 30 carbon atoms. Examples that may be mentioned include octyldodecanol, 2-butyloctanol, 2-hexyldecanol, 2-undecylpentadecanol, oleyl alcohol and linoleyl alcohol.

As regards the esters of a fatty acid and/or of a fatty alcohol, which are advantageously different from the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following may especially be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which contain at least 4 carbon atoms. These sugars may be monosaccharides, oligosaccharides or polysaccharides.

Examples of suitable sugars that may be mentioned include sucrose (or saccharose), glucose, galactose, ribose, fructose, maltose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds.

The esters according to this variant may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, especially, oleo-palmitate, oleo-stearate and palmito-stearate mixed esters.

It is more particularly preferred to use monoesters and diesters and especially sucrose, glucose or methylglucose mono- or dioleates, stearates, behenates, oleopalmitates, linoleates, linolenates and oleostearates.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% di-tri-ester-polyester;
the sucrose mono-dipalmito-stearate sold by the company Goldschmidt under the name Tegosoft® PSE.

The non-silicone wax(es) is (are) chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant sold by the company Bertin (France), animal waxes, for instance beeswaxes, or modified beeswaxes (cerabellina); other waxes or waxy raw materials that may be used according to the invention are especially marine waxes such as the product sold by the company Sophim under the reference M82, and waxes of polyethylene or of polyolefins in general.

The silicones that may be used in the cosmetic compositions of the present invention are volatile or non-volatile, cyclic, linear or branched silicones, which are unmodified or modified with organic groups, having a viscosity from $5 \times 10^{-6}$ to 2.5 m$^2$/s at 25° C., and preferably $1 \times 10^{-5}$ to 1 m$^2$/s.

The silicones that may be used in accordance with the invention may be in the form of oils, waxes, resins or gums.

Preferably, the silicone is chosen from polydialkylsiloxanes, especially polydimethylsiloxanes (PDMS), and organomodified polysiloxanes comprising at least one functional group chosen from poly(oxy-alkylene) groups, amino groups and alkoxy groups.

The organopolysiloxanes are defined in greater detail in Walter Noll's "Chemistry and Technology of Silicones" (1968) Academic Press. They can be volatile or non-volatile.

When they are volatile, the silicones are more particularly chosen from those having a boiling point of between 60° C. and 260° C., and even more particularly from:
(i) cyclic polydialkylsiloxanes containing from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

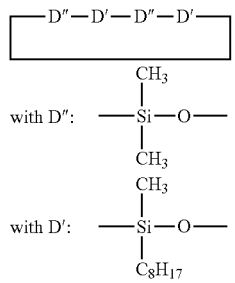

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Non-volatile polydialkylsiloxanes, polydialkylsiloxane gums and resins, polyorganosiloxanes modified with organofunctional groups above, and mixtures thereof, are preferably used.

These silicones are more particularly chosen from polydialkylsiloxanes, among which mention may be made mainly of polydimethylsiloxanes containing trimethylsilyl end groups. The viscosity of the silicones is measured, for example, at 25° C. according to ASTM standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups known under the name Dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly ($C_1$-$C_{20}$) dialkylsiloxanes.

The silicone gums that can be used in accordance with the invention are especially polydialkylsiloxanes and preferably polydimethylsiloxanes with high number-average molecular masses of between 200 000 and 1 000 000, used alone or as a mixture in a solvent. This solvent can be chosen from volatile silicones, polydimethylsiloxane (PDMS) oils, polyphenylmethylsiloxane (PDMS) oils, isoparaffins, polyiso-butylenes, methylene chloride, pentane, dodecane and tridecane, or mixtures thereof.

Products that can be used more particularly in accordance with the invention are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. This product preferably contains 15% SE 30 gum and 85% SF 96 oil.

The organopolysiloxane resins that can be used in accordance with the invention are crosslinked siloxane systems containing the following units:

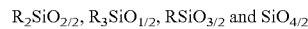

in which R represents an alkyl containing 1 to 16 carbon atoms. Among these products, the ones that are particularly preferred are those in which R denotes a $C_1$-$C_4$ lower alkyl radical, more particularly methyl.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of the trimethyl siloxysilicate type resins sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based radical.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen particularly from linear and/or branched polydimethyl/methylphenyl-siloxanes and polydimethyl/diphenylsiloxanes with viscosity of from $1\times10^{-5}$ to $5\times10^{-2}$ m$^2$/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;

alkoxylated groups such as the product sold under the name Silicone Copolymer F-755 by SWS Silicones, and Abil Wax® 2428, 2434 and 2440 by the company Goldschmidt.

More particularly, the fatty substances are chosen from compounds that are liquid or pasty at room temperature and at atmospheric pressure.

Preferably, the fatty substance(s) do(es) not comprise(s) any $C_2$-$C_3$ oxyalkylene units or any glycerolated units.

Preferably, the fatty substance is a compound that is liquid at a temperature of 25° C. and at atmospheric pressure.

The fatty substances are preferably chosen from $C_6$-$C_{16}$ lower alkanes, fatty alcohols other than fatty alcohols that are solid at ambient temperature, esters of a fatty acid and/or of a fatty alcohol, oils, in particular mineral or synthetic non-silicone oils, silicones, or mixtures thereof.

More advantageously, the fatty substances are chosen from $C_6$-$C_{16}$ lower alkanes, fatty alcohols other than fatty alcohols that are solid at ambient temperature, esters of a fatty acid and/or of a fatty alcohol, mineral or synthetic non-silicone oils, or mixtures thereof.

Preferably, the fatty substance is chosen from liquid petroleum jelly, polydecenes, and liquid esters of a fatty acid or of a fatty alcohol, or mixtures thereof.

The composition according to the invention may optionally comprise one or more dyes chosen from oxidation dyes, direct dyes or mixtures thereof which will be explained in detail below.

Preferably, the composition according to the invention comprises one or more oxidation dyes.

The oxidation dyes are generally chosen from one or more oxidation bases optionally combined with one or more couplers.

The oxidation bases are chosen, for example, from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloro-aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)-pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis (4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]-pyridine oxidation bases or addition salts thereof described, for example, in patent application FR 2 801 308. Examples that may be mentioned include pyrazolo[1,5-a]pyrid-3-ylamine, 2-acetylaminopyrazolo-[1,5-a]pyrid-3-ylamine, 2-morpholin-4-ylpyrazolo[1,5-a]-pyrid-3-ylamine, 3-aminopyrazolo[1,5-a] pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo-[1,5-a]pyrid-7-yl)ethanol, (3-aminopyrazolo[1,5-a]-pyrid-2-yl)methanol, 3,6-diaminopyrazolo[1,5-a]-pyridine, 3,4-diaminopyrazolo[1,5-a]pyridine, pyrazolo-[1,5-a]pyridine-3,7-diamine, 7-morpholin-4-ylpyrazolo-[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo-[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxy-methylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazoles that may also be mentioned include diamino-N, N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H, 5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylamino-pyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

The composition according to the invention may optionally comprise one or more couplers advantageously chosen from those conventionally used in the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxy-benzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]-benzimidazole, the addition salts thereof with an acid, and mixtures thereof.

In general, the addition salts of the oxidation bases and couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.0001% to 10% by weight relative to the total weight of the composition, and preferably from 0.005% to 5% by weight relative to the total weight of the composition.

The content of coupler(s), if it is (they are) present, each advantageously represent from 0.0001% to 10% by weight relative to the total weight of the composition, and preferably from 0.005% to 5% by weight relative to the total weight of the composition.

The composition according to the invention may optionally comprise, preferably in addition to the oxidation dye(s), one or more synthetic or natural direct dyes, chosen from ionic and nonionic species, preferably cationic or nonionic species.

As examples of direct dyes that are suitable for use, mention may be made of azo; methine; carbonyl; azine; nitro (hetero)aryl; tri(hetero)arylmethane; porphyrin; phthalocyanine direct dyes; and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. It is also possible to use extracts or decoctions containing these natural dyes and especially henna-based poultices or extracts.

When they are present, the direct dye(s) more particularly represent(s) from 0.0001% to 10% by weight and preferably from 0.005% to 5% by weight relative to the total weight of the composition.

The composition according to the invention also comprises one or more oxidizing agents.

More particularly, the oxidizing agent(s) is (are) chosen from hydrogen peroxide, urea peroxide, alkali metal bromates or ferricyanides, peroxygenated salts, for instance alkali metal or alkaline-earth persulfates, perborates and percarbonates, and peracids and precursors thereof.

Preferably, the oxidizing agent is not chosen from peroxygenated salts.

Advantageously, the oxidizing agent is hydrogen peroxide.

The content of oxidizing agent(s) more particularly represents from 0.1% to 20% by weight and preferably from 0.5% to 10% by weight relative to the weight of the composition.

The composition according to the invention may also comprise one or more basifying agents.

The basifying agent may be mineral or organic or hybrid.

The mineral basifying agent(s) is (are) preferably chosen from aqueous ammonia, alkali metal carbonates or bicarbonates such as sodium or potassium carbonates or bicarbonates, sodium hydroxide and potassium hydroxide, and mixtures thereof.

The organic basifying agent(s) is (are) preferably chosen from organic amines whose pKb at 25° C. is less than 12, preferably less than 10 and even more advantageously less than 6. It should be noted that it is the pKb corresponding to the function of highest basicity. Moreover, the organic amines do not comprise an alkyl or alkenyl fatty chain comprising more than ten carbon atoms.

The organic basifying agent(s) is (are) chosen, for example, from alkanolamines, oxyethylenated and/or oxypropylenated ethylenediamines, amino acids and the compounds of formula (I) below:

$$\begin{array}{c} R_x \\ \diagdown \\ N-W-N \\ \diagup \\ R_y \end{array} \begin{array}{c} R_z \\ \diagup \\ \diagdown \\ R_t \end{array} \quad (I)$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical, are also suitable for use.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as mono-, di- or tri-alkanolamines comprising from one to three identical or different $C_1$-$C_4$ hydroxyalkyl radicals are in particular suitable for performing the invention.

Among the compounds of this type, mention may be made of monoethanolamine, diethanolamine, triethanolamine, monoisopropanolamine, diisopropanol-amine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in L, D or racemic form, and comprise at least one acid function chosen more particularly from carboxylic acid, sulfonic acid, phosphonic acid and phosphoric acid functions. The amino acids may be in their neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (II) below:

$$R-CH_2-CH \begin{array}{c} NH_2 \\ \diagup \\ \diagdown \\ CO_2H \end{array} \quad (II)$$

in which R denotes a group chosen from:

[imidazole group]; —$(CH_2)_3NH_2$; —$(CH_2)_2NH_2$;
—$(CH_2)_2NHCONH_2$; —$(CH_2)_2NH-C-NH_2$
                                      $\|$
                                      $NH$ The compounds corresponding to formula (II) are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine may also be chosen from compounds comprising a guanidine function. As amines of this type that may be used in the present invention, besides arginine that has already been mentioned as an amino acid, mention may be made especially of creatine, creatinine, 1,1-dimethylguanidine, 1,1-diethyl-guanidine, glycocyamine, metformin, agmatine, N-amidinoalanine, 3-guanidinopropionic acid, 4-guanidino-butyric acid and 2-([amino(imino)methyl]amino)ethane-1-sulfonic acid.

Preferably, the organic amine present in the composition of the invention is an alkanolamine.

Even more preferentially, the organic amine is monoethanolamine.

Hybrid compounds that may be mentioned include salts of the amines mentioned previously with acids such as carbonic acid or hydrochloric acid.

Guanidine carbonate or monoethanolamine hydrochloride may be used in particular.

Advantageously, the composition according to the invention has a content of basifying agent(s) ranging from 0.01% to 30% by weight and preferably from 0.1% to 20% by weight relative to the weight of the said composition.

According to a particular embodiment, the composition according to the invention preferably does not comprise any aqueous ammonia or salt thereof as basifying agent. According to this particular embodiment, if, however, it did contain any, its content would not exceed 0.03% by weight (expressed as $NH_3$) and would preferably not exceed 0.01% by weight relative to the weight of the composition according to the invention. Preferably, if the composition comprises aqueous ammonia or a salt thereof, then the amount of basifying agent(s) is greater than that of aqueous ammonia (expressed as $NH_3$).

The composition according to the invention advantageously contains one or more basifying agents.

The composition of the invention preferably contains one or more alkanolamines and/or one or more basic amino acids.

Preferably, the composition of the invention contains monoethanolamine.

The composition according to the invention may also comprise one or more surfactants.

Preferably, the surfactant(s) is (are) chosen from nonionic surfactants or from anionic surfactants.

The anionic surfactants are more especially chosen from the salts (in particular alkali metal salts, especially sodium salts, ammonium salts, amine salts, amino alcohol salts or alkaline-earth metal salts such as magnesium salts) of the following compounds:
  alkyl sulfates, alkyl ether sulfates, alkylamido ether sulfates, alkylaryl polyether sulfates, monoglyceride sulfates;
  alkylsulfonates, alkylamidesulfonates, alkylaryl-sulfonates, α-olefin sulfonates, paraffin sulfonates;
  alkyl phosphates, alkyl ether phosphates;
  alkylsulfosuccinates, alkyl ether sulfosuccinates, alkylamidesulfosuccinates; alkylsulfosuccinamates;
  alkylsulfoacetates;
  acylsarcosinates; acylisethionates and N-acyl-taurates;
  salts of fatty acids such as oleic acid, ricinoleic acid, palmitic acid or stearic acid, coconut oil acid or hydrogenated coconut oil acid;
  alkyl-D-galactoside uronic acid salts;
  acyllactylates;
  salts of polyoxyalkylenated alkyl ether carboxylic acids, of polyoxyalkylenated alkylaryl ether carboxylic acids or of polyoxyalkylenated alkylamido ether carboxylic acids, in particular those containing from 2 to 50 ethylene oxide groups;
  and mixtures thereof.

It should be noted that the alkyl or acyl radical of these various compounds advantageously contains from 6 to 24 carbon atoms and preferably from 8 to 24 carbon atoms, and the aryl radical preferably denotes a phenyl or benzyl group.

The nonionic surfactants are more particularly chosen from monooxyalkylenated or polyoxyalkylenated nonionic surfactants and from monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:
  oxyalkylenated ($C_8$-$C_{24}$)alkylphenols,
  saturated or unsaturated, linear or branched, oxyalkylenated $C_8$-$C_{30}$ alcohols,
  saturated or unsaturated, linear or branched, oxyalkylenated $C_8$-$C_{30}$ amides,
  esters of saturated or unsaturated, linear or branched, $C_8$-$C_{30}$ acids and of polyethylene glycols,
  polyoxyethylenated esters of saturated or unsaturated, linear or branched, $C_8$-$C_{30}$ acids and of sorbitol,
  saturated or unsaturated, oxyethylenated plant oils,
  condensates of ethylene oxide and/or of propylene oxide, inter alia, alone or as mixtures.

The surfactants contain a number of moles of ethylene oxide and/or a number of moles of propylene oxide of between 1 and 100, preferably between 2 and 50, and preferably between 2 and 30. Advantageously, the nonionic surfactants do not comprise any oxypropylene units.

In accordance with one preferred embodiment of the invention, the oxyalkylenated nonionic surfactants are chosen from oxyethylenated $C_8$-$C_{30}$ alcohols comprising from 1 to 100 moles of ethylene oxide; polyoxyethylenated esters of saturated or unsaturated, linear or branched, $C_8$-$C_{30}$ acids and of sorbitol comprising from 1 to 100 moles of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

$$RO—[CH_2—CH(CH_2OH)—O]_m—H$$

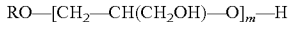

in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferably, the surfactant present in the composition is a nonionic surfactant.

The content of surfactants in the composition more particularly represents from 0.1% to 50% by weight and preferably from 0.5% to 30% by weight relative to the weight of the composition.

The composition may also contain various adjuvants conventionally used in hair dye compositions, such as anionic, cationic, nonionic, amphoteric or zwitterionic polymers or mixtures thereof; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of composition.

The composition may comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkyl aryl sulfonates and amine oxides, and mixtures thereof.

Organophilic clays that may be mentioned include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst and Claytone AF and Claytone APA by the company Southern Clay; quaternium-18/benzalkonium bentonites such as those sold under the names Claytone HT and Claytone PS by the company Southern Clay, quaternium-18 hectorites such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by the company Rheox, and Simagel M and Simagel SI 345 by the company Biophil.

The fumed silicas may be obtained by high-temperature hydrolysis of a volatile silicon compound in an oxhydric flame, producing a finely divided silica. This process makes it possible especially to obtain hydrophilic silicas having a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the said silica, via a chemical reaction generating a reduction in the number of silanol groups. It is especially possible to substitute silanol groups with hydrophobic groups: a hydrophobic silica is then obtained.

The hydrophobic groups may be.
trimethylsiloxyl groups, which are obtained especially by treating fumed silica in the presence of hexamethyldisilazane. Silicas thus treated are known as "silica silylate" according to the CTFA (6th Edition, 1995). They are sold, for example, under the references Aerosil R812® by the company Degussa and Cab-O-Sil TS-530® by the company Cabot;
dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener represents from 1% to 30% by weight relative to the weight of the composition.

The composition may also comprise one or more organic thickeners.

These thickeners may be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to one particular embodiment, the organic thickener is chosen from cellulose-based thickeners (hydroxyethylcellulose, hydroxypropyl-cellulose or carboxymethylcellulose), guar gum and derivatives thereof (hydroxypropyl guar), gums of microbial origin (xanthan gum, scleroglucan gum) and acrylic acid or acrylamidopropanesulfonic acid crosslinked homopolymers, and preferably from cellulose-based thickeners in particular with hydroxyethylcellulose.

The content of organic thickener(s), if they are present, usually ranges from 0.01% to 20% by weight and preferably from 0.1% to 5% by weight relative to the weight of the composition.

The cosmetically acceptable medium of the composition according to the invention is a medium comprising water and optionally one or more organic solvents.

Examples of organic solvents that may be mentioned include linear or branched and preferably saturated monoalcohols or diols, containing 2 to 10 carbon atoms, such as ethyl alcohol, isopropyl alcohol, hexylene glycol(2-methyl-2,4-pentanediol), neopentyl glycol and 3-methyl-1,5-pentanediol; aromatic alcohols such as benzyl alcohol and phenylethyl alcohol; glycerol; polyols or polyol ethers, for instance ethylene glycol monomethyl, monoethyl and monobutyl ethers, 2-butoxyethanol, propylene glycol or ethers thereof, for instance propylene glycol, butylene glycol or dipropylene glycol monomethyl ether; and also diethylene glycol alkyl ethers, especially of $C_1$-$C_4$, for instance diethylene glycol monoethyl ether or monobutyl ether, alone or as a mixture.

The solvents, when they are present, generally represent between 1% and 40% by weight relative to the total weight of the dye composition, and preferably between 5% and 30% by weight relative to the total weight of the dye composition.

Preferably, the composition of the invention contains water in a content ranging from 10% to 70% and better still from 20% to 55% of the total weight of the composition.

The dye composition according to the invention may be in various forms, such as in the form of liquids, creams or gels, or in any other form that is suitable for dyeing keratin fibres, and especially human hair.

Advantageously, the composition according to the invention is in the form of a gel or a cream.

The pH of the composition according to the invention is advantageously between 3 and 12, preferably between 5 and 11 and preferentially between 7 and 11, limits inclusive.

It may be adjusted to the desired value by means of acidifying or basifying agents usually used in the dyeing of keratin fibres, or alternatively using standard buffer systems.

The alkaline agents are, for example, those described previously.

Examples of acidifying agents that may be mentioned include mineral or organic acids, for instance hydrochloric acid, orthophosphoric acid, carboxylic acids, for instance tartaric acid, citric acid or lactic acid, or sulfonic acids.

The composition of the invention may be obtained by mixing at least two or even three different compositions, or optionally more than three different compositions. One or more of the compositions leading, by mixing, to the composition of the invention may be anhydrous.

The expression "anhydrous compositions" is understood more particularly to mean compositions for which the water content is equal to 0 or less than 5% by weight, preferably less than 2% by weight and more particularly still less than 1% by weight, relative to the weight of said composition. It should be noted that the water may also be in the form of bound water, such as the water of crystallization of salts or traces of water absorbed by the raw materials used in the production of the compositions according to the invention.

It should be noted that the composition according to the invention is prepared just before being applied to the human keratin fibres.

According to a first variant, the composition according to the invention is obtained by mixing a first composition comprising one or more fatty substances, optionally one or more dyes, preferably oxidation dyes, with a second composition comprising one or more oxidizing agent(s), the first composition and/or the second composition comprising at least one fatty alcohol that is solid at ambient temperature, and the first composition and/or the second composition comprising the optional basifying agent(s), the latter preferably being in the first composition.

According to a second variant of the invention, the composition according to the invention is obtained by mixing a first composition comprising one or more fatty substances, a second composition comprising one or more oxidation dyes and a third composition comprising one or more oxidizing agent(s), the first and/or second and/or third composition comprising at least one fatty alcohol that is solid at ambient temperature, the first and/or second and/or third composition comprising the optional basifying agent(s), the latter preferably being in the first and/or second composition. The first composition may in particular be anhydrous.

According to another variant of the invention, the composition for lightening according to the invention is obtained by mixing a first composition comprising one or more fatty substances, a second composition comprising one or more basifying agents, and a third composition comprising one or more oxidizing agents, the first and/or second and/or third composition comprising at least one fatty alcohol that is solid at ambient temperature. The first composition may in particular be anhydrous.

The ingredients of the abovementioned compositions and the contents thereof are determined as a function of the characteristics detailed previously for the final composition according to the invention.

In each of the abovementioned variants, the oxidizing composition is preferably an aqueous composition. In particular, it comprises more than 5% by weight of water, preferably more than 10% by weight of water and even more advantageously more than 20% by weight of water.

It may also comprise one or more organic solvents chosen from those listed previously; these solvents more particularly representing, when they are present, from 1% to 40% by weight and preferably from 5% to 30% by weight relative to the weight of the oxidizing composition.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Usually, the pH of the oxidizing composition, when it is aqueous, is less than 7.

Preferably, the oxidizing composition comprises hydrogen peroxide as oxidizing agent, in aqueous solution, the concentration of which varies, more particularly, from 0.1 to 50%, more particularly between 0.5 and 20%, and more preferably still between 1 and 15% by weight relative to the weight of the oxidizing composition.

The dyeing process according to the invention thus consists in applying the composition according to the invention to wet or dry human keratin fibres.

The composition is then left in place for a time usually ranging from one minute to one hour and preferably from 5 minutes to 30 minutes.

The temperature during the process is conventionally between room temperature (between 15 and 25° C.) and 80° C., preferably between room temperature and 60° C.

After the treatment, the human keratin fibres are optionally rinsed with water, optionally washed with a shampoo and then rinsed with water, before being dried or left to dry.

The invention relates to a two-compartment device comprising, in one compartment, a first composition comprising one or more fatty substances, optionally one or more dyes, preferably oxidation dyes, and in the other compartment, a second composition comprising one or more oxidizing agents; the first composition and/or the second composition comprising at least one fatty alcohol that is solid at ambient temperature and optionally one or more basifying agents, the latter preferably being in the first composition; the two compartments being intended to be mixed in order to give the composition according to the invention, just before application to the human keratin fibres.

The invention also relates to a two-compartment device comprising, in one compartment, a first composition comprising one or more fatty substances, one or more dyes, preferably oxidation dyes, and in the other compartment, a second composition comprising one or more oxidizing agents; the first composition and/or the second composition comprising at least one fatty alcohol that is solid at ambient temperature and optionally one or more basifying agents, the latter preferably being in the first composition; the compositions of the two compartments being intended to be mixed in order to give the composition according to the invention, just before application to the human keratin fibres.

It also relates to a three-compartment device comprising, in one compartment, a first composition comprising one or more fatty substances, in another compartment, a second composition comprising one or more dyes, preferably oxidation dyes, and in the last compartment, a third composition comprising one or more oxidizing agents; the first and/or second and/or third composition comprising at least one fatty alcohol that is solid at ambient temperature and optionally one or more basifying agents, the latter preferably being in the first or the second composition; the compositions of the three compartments being intended to be mixed in order to give the composition according to the invention, just before application to the human keratin fibres.

It furthermore relates to a three-compartment device comprising, in one compartment, a first composition comprising one or more fatty substances, in another compartment, a second composition comprising one or more basifying agents, and in the last compartment, a third composition comprising one or more oxidizing agents; the first, second and/or third composition comprising at least one fatty alcohol that is solid at ambient temperature; the three compartments being intended to be mixed in order to give the composition according to the invention, just before application to the human keratin fibres. It should be noted that the second composition does not comprise any dyes.

The example that follows serves to illustrate the invention without, however, being limiting in nature.

EXAMPLE 1

The following compositions are prepared (the amounts are expressed in g % of active material):

| Composition 1 | |
|---|---|
| Disteardimonium hectorite (Bentone 38 VCG) | 3 |
| Octyldodecanol | 11.5 |
| Glycol distearate | 8 |
| Liquid petroleum jelly | 64.5 |
| Propylene carbonate | 1 |
| Laureth-2 | 1 |
| Polysorbate 21 | 11 |

| Composition 2 | |
|---|---|
| Pentasodium pentetate | 1 |
| Sodium meta bisulfite | 0.7 |
| Monoethanolamine | 14.5 |
| 2,5-Toluenediamine | 2.25 |
| 2,4-Diaminophenoxyethanol hydrochloride | 0.05 |
| Resorcinol | 2 |
| m-Aminophenol | 0.36 |
| Hydroxyethylcellulose (Natrosol 250 HHR, Aqualon) | 1.5 |
| Hexylene glycol | 3 |
| Dipropylene glycol | 3 |
| Ethanol | 8.25 |
| Propylene glycol | 6.2 |
| Ascorbic acid | 0.25 |
| Water | qs 100 |

| Composition 3 | |
|---|---|
| Pentasodium pentetate | 0.15 |
| Hydrogen peroxide (aqueous 50% solution) | 12 |
| Sodium stannate | 0.04 |
| Phosphoric acid | qs pH 2.2 |
| Tetrasodium pyrophosphate | 0.03 |
| Liquid petroleum jelly | 20 |
| Tetramethyl hexamethylenediamine/1,3-dichloropropylene polycondensate (aqueous 40% solution; Hexadimethrine chloride) | 0.1 |
| Polydimethyldiallylammonium chloride (non-stabilized aqueous 40% solution, Polyquaternium-6) | 0.2 |
| Glycerol | 0.5 |
| Cetylstearyl alcohol (C16/C18 30/70 - NAFOL 1618 F) | 8 |
| Oxyethylenated cetylstearyl alcohol (33 EO) | 3 |
| Oxyethylenated rapeseed acid amide (4 EO) | 1.2 |
| Vitamin E: DL-α-tocopherol | 0.1 |
| Water | qs 100 |

Mode of Application

The three compositions detailed above are mixed together at the time of use in the following proportions:

10 g of composition 1,
4 g of composition 2,
16 g of composition 3.

The resulting mixture is then applied to locks of natural grey hair containing 90% white hairs, at a rate of 10 g of mixture per 1 g of hair.

The mixture is left on at room temperature for 30 minutes.

The hair is then rinsed, washed with a standard shampoo and dried.

Light chestnut-brown locks are obtained (visual evaluation).

EXAMPLE 2

The procedure from Example 1 was followed, by using compositions 1 and 3, composition 2 being the following:

| Composition 2 | |
|---|---|
| Pentasodium pentetate | 1 |
| Sodium meta bisulfite | 0.7 |
| Monoethanolamine | 14.5 |
| Hydroxyethylcellulose (Natrosol 250 HHR, Aqualon) | 1.5 |
| Hexylene glycol | 3 |
| Dipropylene glycol | 3 |
| Ethanol | 8.25 |
| Propylene glycol | 6.2 |
| Ascorbic acid | 0.25 |
| Water | qs 100 |

Mode of Application

The abovementioned three compositions are mixed together at the time of use in the following proportions:

10 g of composition 1,
4 g of composition 2,
16 g of composition 3.

The resulting mixture is then applied to locks of natural chestnut hair, at a rate of 10 g of mixture per 1 g of hair.

The mixture is left on at room temperature for 30 minutes.

The hair is then rinsed, washed with a standard shampoo and dried.

Dark blonde locks with golden tints are obtained (visual evaluation).

The invention claimed is:

1. A composition for dyeing or lightening human keratin fibers, comprising, in a cosmetically acceptable medium:
  (a) at least 25% by weight of a mixture of fatty substances comprising at least one fatty alcohol that is solid at ambient temperature (25° C.); and at least one additional fatty substance chosen from $C_6$-$C_{16}$ lower alkanes, non-silicone oils of animal, mineral or synthetic origin, fatty alcohols other than fatty alcohols that are solid at ambient temperature, esters of a fatty acid, esters of a fatty alcohol, non-silicone waxes, and silicones;
  (b) at least one oxidizing agent;
  (c) optionally at least one basifying agent; and
  (d) water in an amount ranging from 10% to less than 55% by weight, relative to the weight of the composition.

2. The composition according to claim 1, wherein the at least one fatty alcohol that is solid at ambient temperature is chosen from saturated $C_3$-$C_{30}$ linear alcohols.

3. The composition according to claim 2, wherein the at least one fatty alcohol that is solid at ambient temperature is chosen from cetyl alcohol and stearyl alcohol.

4. The composition according to claim 1, wherein the at least one fatty alcohol that is solid at ambient temperature is present in the composition in an amount ranging from 0.2% to 50% by weight, relative to the weight of the composition.

5. The composition according to claim 1, wherein the at least one additional fatty substance other than fatty alcohols that are solid at ambient temperature, are chosen from compounds that are liquid or pasty.

6. The composition according to claim 5, wherein the at least one additional fatty substance other than fatty alcohols that are solid at ambient temperature, are chosen from compounds that are liquid at ambient temperature and at atmospheric pressure.

7. The composition according to claim 1, wherein the at least one additional fatty substance other than fatty alcohols that are solid at ambient temperature, are chosen from $C_6$-$C_{16}$ lower alkanes, non-silicone oils of plant, mineral or synthetic origin, fatty alcohols other than fatty alcohols that are solid at ambient temperature, fatty acids, esters of a fatty acid, and esters of a fatty alcohol.

8. The composition according claim 1, wherein the total content of the mixture of fatty substances is present in the composition in an amount ranging from 25% to 80% by weight, relative to the weight of the composition.

9. The composition according to claim 1, further comprising at least one oxidation dye chosen from para-phenylenediamines, bisphenylalkylenediamines, para-aminophenols, ortho-aminophenols, heterocyclic bases, and the addition salts thereof.

10. The composition according to claim 9, further comprising at least one coupler chosen from meta-phenylenediamines, meta-aminophenols, meta-diphenols, naphthalene-based couplers and heterocyclic couplers, and the addition salts thereof.

11. The composition according to claim 1, further comprising at least one direct dye chosen from ionic and nonionic azo dyes, methine dyes, carbonyl dyes, azine dyes, nitro (hetero) aryl dyes, tri(hetero)arylmethane dyes, porphyrin dyes phthalocyanine dyes and natural direct dyes.

12. The composition according to claim 1, further comprising at least one basifying agent chosen from aqueous ammonia, alkali metal carbonates, alkali metal bicarbonates, sodium hydroxide, potassium hydroxide and organic amines whose pKb at 25° C. is less than 12.

13. The composition according to claim 12, wherein the at least one basifying agent is an organic amine chosen from alkanol amines.

14. The composition according to claim 13, wherein the at least one basifying agent is monoethanolamine.

15. The composition according to claim 12, wherein the at least one basifying agent is an organic amine chosen from basic amino acids.

16. The composition according to claim 15, wherein the organic amine is chosen from arginine, histidine, and lysine.

17. A process for dyeing or lightening human keratin fibers, comprising applying to human keratin fibers a composition comprising, in a cosmetically acceptable medium:
   (a) at least 25% by weight of a mixture of fatty substances comprising at least one fatty alcohol that is solid at ambient temperature (25° C.), and at least one additional fatty substance chosen from $C_6$-$C_{16}$ lower alkanes, non-silicone oils of animal, mineral or synthetic origin, fatty alcohols other than fatty alcohols that are solid at ambient temperature, esters of a fatty acid, esters of a fatty alcohol, non-silicone waxes, and silicones;
   (b) at least one oxidizing agent; and
   (c) optionally at least one basifying agent; and
   (d) water in an amount ranging from 10% to less than 55% by weight, relative to the weight of the composition.

18. A two-compartment device comprising, in one compartment, a first composition comprising at least 25% by weight of a mixture of fatty substances comprising at least one fatty alcohol that is solid at ambient temperature (25° C.), and at least one additional fatty substance chosen from $C_6$-$C_{16}$ lower alkanes, non-silicone oils of animal, mineral or synthetic origin, fatty alcohols other than fatty alcohols that are solid at ambient temperature, esters of a fatty acid, esters of a fatty alcohol, non-silicone waxes, and silicones,
   and in the second compartment, a second composition comprising at least one oxidizing agent; wherein the first composition and/or the second optionally comprise at least one basifying agent;
   and wherein the compositions of the two compartments are mixed just before application to the human keratin fibers; and
   wherein the amount of water present in the mixed composition ranges from 10% to less than 55% by weight, relative to the weight of the composition.

19. A two-compartment device comprising, in one compartment, a first composition comprising at least 25% by weight of a mixture of fatty substances comprising at least one fatty alcohol that is solid at ambient temperature (25° C.), and at least one additional fatty substance chosen from $C_6$-$C_{16}$ lower alkanes, non-silicone oils of animal, mineral or synthetic origin, fatty alcohols other than fatty alcohols that are solid at ambient temperature, esters of a fatty acid, esters of a fatty alcohol, non-silicone waxes, and silicones; and at least one basifying agent,
   and in the second compartment, a second composition comprising at least one oxidizing agent;
   and wherein the compositions of the two compartments are mixed just before application to the human keratin fibers; and
   wherein the amount of water present in the mixed composition ranges from 10% to less than 55% by weight, relative to the weight of the composition.

20. A three-compartment device comprising, in one compartment, a first composition comprising at least one fatty substance, in another compartment, a second composition comprising at least one oxidation dye, and in the last compartment, a third composition comprising at least one oxidizing agent;
   the first, second and/or third composition comprising at least one fatty alcohol that is solid at ambient temperature (25° C.), and at least one additional fatty substance chosen from $C_6$-$C_{16}$ lower alkanes, non-silicone oils of animal, mineral or synthetic origin, fatty alcohols other than fatty alcohols that are solid at ambient temperature, esters of a fatty acid, esters of a fatty alcohol, non-silicone waxes, and silicones and optionally at least one basifying agent
   wherein the total amount of the mixture of fatty substances is at least 25% by weight;
   and wherein the compositions of the three compartments are mixed just before application to the human keratin fibers; and
   wherein the amount of water present in the mixed composition ranges from 10% to less than 55% by weight, relative to the weight of the composition.

21. A three-compartment device comprising, in one compartment, a first composition comprising at least one fatty substance, in another compartment, a second composition comprising at least one basifying agent, and in the last compartment, a third composition comprising at least one oxidizing agent;
   the first, second and/or third composition comprising at least one fatty alcohol that is solid at ambient temperature (25° C.), and at least one additional fatty substance chosen from $C_6$-$C_{16}$ lower alkanes, non-silicone oils of animal, mineral or synthetic origin, fatty alcohols other than fatty alcohols that are solid at ambient temperature, esters of a fatty acid, esters of a fatty alcohol, non-silicone waxes, and silicones;

wherein the total amount of the mixture of fatty substances is at least 25% by weight;

and wherein the compositions of the three compartments are mixed just before application to the human keratin fibers; and wherein the amount of water present in the mixed composition ranges from 10% to less than 55% by weight, relative to the weight of the composition.

22. The composition according to claim 4, wherein the at least one fatty alcohol that is solid at ambient temperature is present in the composition in an amount ranging from 1% to 15% by weight, relative to the weight of the composition.

23. The composition according claim 8, wherein the total content of the mixture of fatty substances is present in the composition in an amount ranging from 30% to 55% by weight, relative to the weight of the composition.

24. The composition according to claim 12, further comprising at least one basifying agent chosen from aqueous ammonia, alkali metal carbonates, alkali metal bicarbonates, sodium hydroxide, potassium hydroxide and organic amines whose pKb at 25° C. is less than 6.

* * * * *